United States Patent [19]
Del Rossi et al.

[11] Patent Number: 5,107,047
[45] Date of Patent: Apr. 21, 1992

[54] ZEOLITE MCM-22 CATALYSTS FOR OLEFIN ISOMERIZATION

[75] Inventors: Kenneth J. Del Rossi, Mantua, N.J.; Albin Huss, Jr., Chadds Ford, Pa.

[73] Assignee: Mobil Oil Corporation, Fairfax, Va.

[21] Appl. No.: 649,115

[22] Filed: Jan. 28, 1991

Related U.S. Application Data

[63] Continuation-in-part of Ser. No. 571,386, Aug. 23, 1990, abandoned.

[51] Int. Cl.$^5$ .............................................. C07C 5/23
[52] U.S. Cl. ..................................... 585/666; 585/664
[58] Field of Search ................................. 585/666, 664

[56] References Cited

U.S. PATENT DOCUMENTS

| | | | |
|---|---|---|---|
| 4,324,940 | 4/1982 | Dessau | 585/666 |
| 4,439,409 | 3/1984 | Puppe et al. | 502/60 |
| 4,749,819 | 6/1988 | Hamilton, Jr. | 585/329 |
| 4,777,322 | 10/1988 | Hoelderich et al. | 585/666 |
| 4,826,667 | 5/1989 | Zones et al. | 423/277 |
| 4,954,325 | 9/1990 | Rubin et al. | 423/328 |
| 4,956,514 | 9/1990 | Chu | 585/533 |
| 4,962,250 | 10/1990 | Dessau et al. | 585/417 |

FOREIGN PATENT DOCUMENTS

| | | |
|---|---|---|
| 1222529 | 2/1987 | Canada. |
| 0247802 | 6/1984 | European Pat. Off.. |

Primary Examiner—Anthony McFarlane
Assistant Examiner—Nhat Phau
Attorney, Agent, or Firm—Alexander J. McKillop; Charles J. Speciale; Marina V. Schneller

[57] ABSTRACT

The invention is a catalytic process for isomerizing an olefin under catalytic isomerization conditions, in the presence of an olefin isomerization catalyst comprising MCM-22. The light olefins are linear and/or branched olefins containing greater than three carbon atoms. The olefins can be contained in a fraction having a boiling range of from $C_5+$ to 390° F.

50 Claims, 2 Drawing Sheets

ZEOLITE MCM-22 CATALYSTS FOR OLEFIN ISOMERIZATION

This is a continuation-in-part of copending application Ser. No. 571,386, filed on Aug. 23, 1990, now abandoned.

FIELD OF THE INVENTION

The invention relates to catalytic olefin isomerization in the presence of a catalyst comprising MCM-22. The catalytic process of the invention includes both double bond and skeletal isomerization.

One aspect of the invention relates to a double bond isomerization process for movement of a double bond possessed by an olefinic molecule, from an alpha position to an interior position in the molecule, which process comprises contacting at least one olefin having an alpha double bond therein with a catalyst composition comprising MCM-22 under catalytic process conditions.

Another aspect of the invention relates to improvement of the octane of olefin rich gasolines, such as light FCC gasolines. Double bond and/or skeletal isomerization of linear and/or branched olefin components of olefin rich gasoline to higher octane isomers results in upgrading the gasoline.

BACKGROUND OF THE INVENTION

Olefins are important intermediates in the manufacture of many commodity petrochemicals. For instance, high octane gasoline is produced on a large scale by alkylation of isoparaffins, such as isobutane or isopentane, with olefins, such as propylene or butenes. In HF alkylation, the secondary butene isomer, 2-butene, gives a higher octane alkylate than 1-butene, and is therefore the preferred feed.

The four $C_4$ mono-olefins, 1-butene, cis-2-butene, trans-2-butene and 2-methylpropene are collectively called butylenes. The term isobutylene is by established usage interchangeable with the nomenclature 2-methylpropene, while the other three isomers are n-butenes. Often they are treated collectively because the four mono-olefins are obtained as mixtures, from natural gas and from petroleum refinery processes. The $C_4$ olefins are often contained in mixtures of $C_1$–$C_5$ hydrocarbons, which include both alkanes and alkenes.

One object of the invention is to convert n-butene(s) to 2-butene. An object of the process is to produce 2-butene with high selectivity.

Another object of the process of this invention is to convert n-butenes to isobutylene. Isobutylene is a desirable reactant for the production of alkylate, which includes high octane gasoline components, and for the production of methyl-t-butyl ether, when isobutylene is reacted with methanol. A conventional process for separation of isobutylene from the other three components involves sulfuric acid extraction or selective adsorption, as the isomers cannot be separated by simple extraction. Acid extraction is cumbersome and includes as an undesirable aspect the oligomerization of the components themselves.

SUMMARY OF THE INVENTION

The present invention relates to the use of MCM-22 containing catalysts for upgrading light olefins by double bond and/or skeletal isomerization, under catalytic isomerization conditions. The light olefins are linear and/or branched olefins containing greater than three carbon atoms. The olefins can be contained in a refinery light gas stream such as LPG or in a fraction having a boiling range of from $C_5 +$ to 390° F., such as FCC gasoline

DETAILED DESCRIPTION OF THE INVENTION

Figure 1:
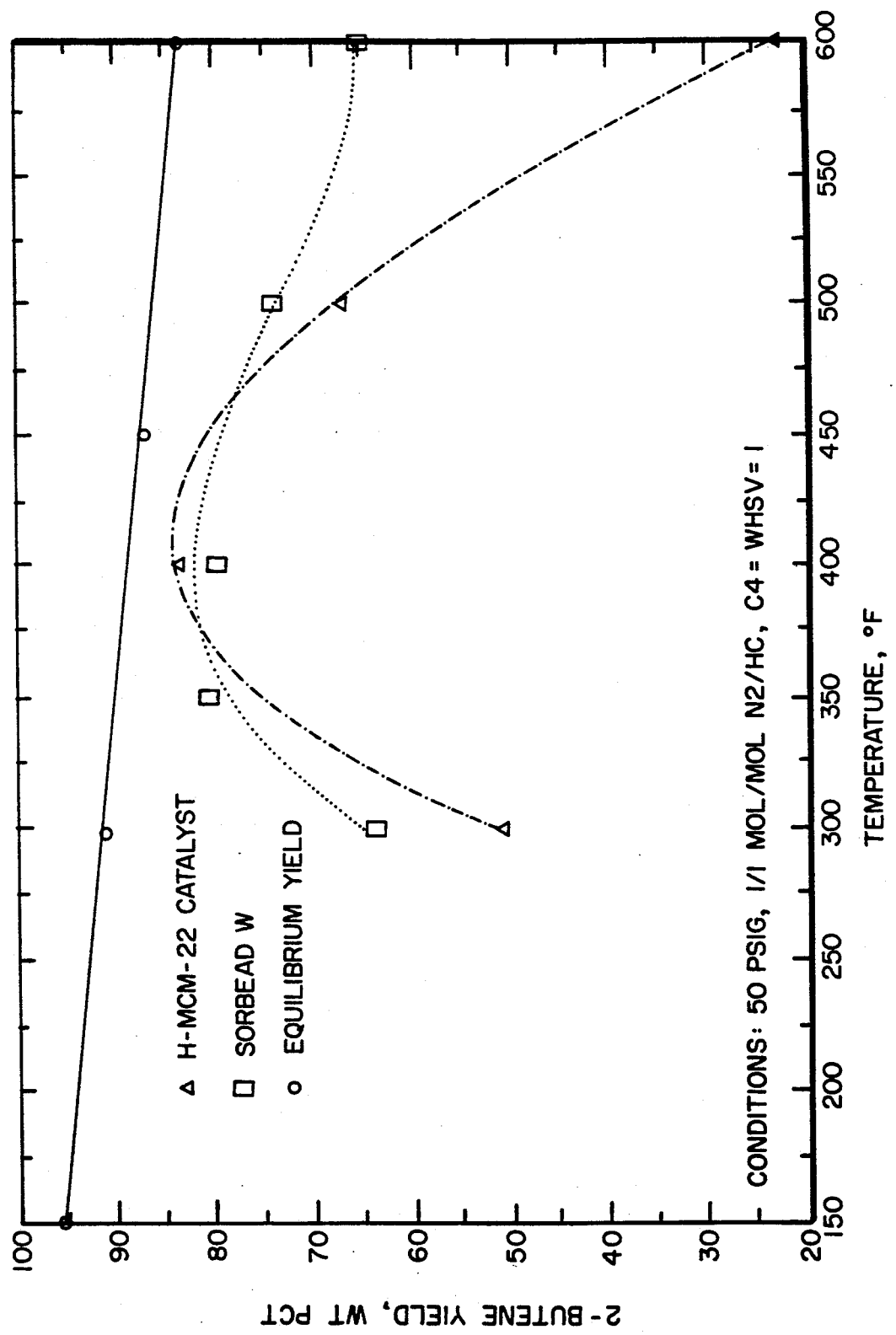
FIG. 1 illustrates the isomerization activity of the catalyst employed in accordance with the invention and is a graph of 2-butene yield vs. temperature.

The invention is a catalytic process for isomerizing an olefin under catalytic isomerization conditions, in the presence of an olefin isomerization catalyst comprising MCM-22. The light olefins are linear and/or branched olefins containing greater than three carbon atoms. The olefins can be contained in a refinery light gas stream such as LPG or in a fraction having a boiling range of from $C_5 +$ to 390° F., such as FCC gasoline. In one embodiment of the invention the olefin is a linear olefin which is sometimes referred as a normal-olefin or a straight chain olefin. In one embodiment of the process, the invention is a catalytic process for isomerizing an olefin having terminal double bond(s), alpha-olefin and/or an omega-olefin, under catalytic isomerization conditions, to an olefin free of terminal double bonds. Moreover, the invention includes isomerizing the olefin to produce an olefinic isomer thereof with the same number of carbon atoms and at least one more tertiary carbon atom.

In the specific embodiment of isomerizing linear and/or branched olefins contained in a fraction having a boiling range of from $C_5+$ to 390° F., the significance of the olefin isomerization reactions can be gleaned from a review of the following table of Octane Numbers of Pure Hydrocarbons from "Catalysis," Vol. VI, P. H. Emmett (ed.) Copyright 1958 by Litton Educational Publishing Company:

| OCTANE NUMBERS OF PURE HYDROCARBONS | |
|---|---|
| Hydrocarbon | Blending Research Octane Number (clear) |
| 1 - hexene | 76 |
| trans-2-hexene | 93 |
| 2-methyl-1-pentene | 94 |
| 2-methyl-2-pentene | 98 |
| 2,3-dimethyl-1-butene | 101 |
| 3,3-dimethyl-1-butene | 112 |

Double bond and/or skeletal isomerization of the linear and branched olefins contained in such a $C_5+$ to 390° F. fraction would result in increased octane values.

The catalytic isomerization conditions include a gas or liquid phase and a temperature of from about 0° C. to about 650° C., a pressure of from about 1.0 psia to about 2000 psia and a weight hourly space velocity of from 0.1 to about 500.

The olefin isomerization catalyst comprises MCM-22. The MCM-22 catalyst herein can be used in intimate combination with a dehydrogenation/hydrogenation component such as tungsten, vanadium, molybdenum, rhenium, nickel, cobalt, chromium, manganese, or a noble metal such as platinum or palladium. Such component can be introduced in the catalyst composition by way of cocrystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing a platinum metal-containing ion. Thus, suitable platinum compounds for this purpose include chloroplatinic acid, platinous chloride and various compounds containing the platinum amine complex.

MCM-22 is readily identified by its characteristic X-ray diffraction pattern. In its calcined form, this synthetic porous crystalline material component employed in the catalyst composition useful in the process of this invention is characterized by an X-ray diffraction pattern including the following lines:

TABLE A

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

Alternatively, it may be characterized by an X-ray diffraction pattern in its calcined form including the following lines:

TABLE B

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines:

TABLE C

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |

TABLE C-continued

| Interplanar d-Spacing (A) | Relative Intensity, $I/I_o \times 100$ |
|---|---|
| 2.99 ± 0.05 | W |
| 2.82 ± 0.05 | W |
| 2.78 ± 0.05 | W |
| 2.68 ± 0.05 | W |
| 2.59 ± 0.05 | W |

Most specifically, it may be characterized in its calcined form by an X-ray diffraction pattern including the following lines:

TABLE D

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensites, 100 $I/I_o$, where $I_o$ is the intensity of the strongest line or peak, and d (obs.) the interplanar spacing in Angstrom Units (A), corresponding to the recorded lines, were determined. In Tables A-D, the relative intensities are given in terms of the symbols W =weak, M =medium, S =strong, VS =very strong. In terms of intensities, these may be generally designated as follows:

W=0-20
M=20-40
S=40-60
VS=60-100

It should be understood that these X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g. silicon to aluminum mole ratio of the particular sample, as well as its degree of thermal treatment.

Examples of such porous crystalline materials include the PSH-3 composition of U.S. Pat. No. 4,439,409, incorporated herein by reference, and MCM-22.

Zeolite MCM-22 has a composition involving the molar relationship:

$$X_2O_3 : (n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O : (1-4)R : X_2O_3 : nYO_2$$

wherein R is an organic component. The Na and R components are associated with the zeolite as a result of their presence during crystallization, and are easily removed by post-crystallization methods hereinafter more particularly described.

Zeolite MCM-22 is thermally stable and exhibits a high surface are greater than about 400 m²/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the olefin isomerization catalyst composition herein without having to first undergo an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof.

In its calcined form, zeolite MCM-22 appears to be made up of a single crystal phase with little or no detectable impurity crystal phases and has an X-ray diffraction pattern including the lines listed in above Tables A-D.

The zeolite, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use in the process of this invention, the zeolite crystals should be dehydrated, at least partially. This can be done by heating the crystals to a temperature in the range of from about 200° C. to about 595° C. in an atmosphere such as air, nitrogen, etc. and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

Zeolite MCM-22 can be prepared from a reaction mixture containing sources of alkali or alkaline earth metal (M), e.g., sodium or potassium, cation, an oxide of trivalent element X, e.g, aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10–60 | 10–40 |
| $H_2O/YO_2$ | 5–100 | 10–50 |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5 |

In a preferred method of synthesizing zeolite MCM-22, the $YO_2$ reactant contains a substantial amount of solid $YO_2$, e.g., at least about 30 wt.% solid $YO_2$. Where $YO_2$ is silica, the use of a silica source containing at least about 30 wt.% solid silica, e.g., Ultrasil (a precipitated, spray dried silica containing about 90 wt.% silica) or HiSil (a precipitated hydrated $SiO_2$ containing about 87 wt.% silica, about 6 wt.% free $H_2O$ and about 4.5 wt.% bound $H_2O$ of hydration and having a particle size of about 0.02 micron) favors crystal formation from the above mixture and is a distinct improvement over the synthesis method disclosed in U.S. Pat. No. 4,439,409. If another source of oxide of silicon, e.g., Q-Brand (a sodium silicate comprised of about 28.8 wt.% of $SiO_2$, 8.9 wt.% $Na_2O$ and 62.3 wt.% $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt.% solid $YO_2$, e.g., silica, and more preferably at least about 40 wt.% solid $YO_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals (based on total weight) of the crystalline product.

The zeolite crystals can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

It may be desired to incorporate the crystalline material with another material which is resistant to the temperatures and other conditions employed in the process of this invention. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. Inactive materials suitably serve as diluents to control the amount of conversion so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with zeolite crystals include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the zeolite also include inorganic oxides, notably alumina.

In addition to the foregoing materials, the crystals can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia. It may also be advantageous to provide at least a part of the foregoing matrix materials in colloidal form so as to facilitate extrusion of the bound catalyst component(s).

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The stability of the catalyst of the invention may be increased by steaming. U.S. Pat. Nos. 4,663,492; 4,594,146; 4,522,929; and 4,429,176, the entire disclosures of which are incorporated herein by reference, describe conditions for the steam stabilization of zeolite catalysts which can be utilized to steam-stabilize the catalyst for use herein. The steam stabilization conditions include contacting the catalyst with, e.g., 5-100% steam at a temperature of at least about 300° C. (e.g., 300°-650° C.) for at least one hour (e.g., 1-200 hours) at a pressure of 101-2,500 kPa. In a more particular embodiment, the catalyst can be made to undergo steaming with 75-100% steam at 315°-500° C. and atmospheric pressure for 2-25 hours. In accordance with the steam stabilization treatment described in the above-mentioned patents, the steaming of the catalyst can take place under conditions sufficient to initially increase the Alpha Value of the catalyst, the significance of which is discussed infra, and produce a steamed catalyst having a peak Alpha Value. If desired, steaming can be continued to subsequently reduce the Alpha Value from the peak Alpha Value to an Alpha Value which is substantially the same as the Alpha Value of the unsteamed catalyst.

The process of this invention can be carried out as a batch-type, semi-continuous or continuous operation utilizing a fixed, fluidized or moving bed catalyst system.

In order to more fully illustrate the process of this invention and the manner of practicing same, the following examples are presented. In the examples illustrative of the synthesis of zeolite, whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM-22 always exhibits Equilibrium Adsorption values of greater than about 10 wt % for water vapor, greater than about 4.5 wt.%, usually greater than about 7 wt.% for cyclohexane vapor and greater than about 10 wt.% for n-hexane vapor. These vapor sorption capacities are a notable distinguishing feature of zeolite MCM-22 and are preferred for the zeolite component of catalyst for use herein.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant =0.016 sec$^{-1}$). The Alpha Test is described in U.S. Pat. 3,354,078, in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

The alpha value of the zeolite MCM-22, based on the molar relationship:

X₂O₃:(n)YO₂, also set forth and defined as above, in which X is aluminum, will exhibit, in the acid or protonated form, an alpha value of from about 100 to 300. The alpha value of the zeolite MCM-22, based on the molar relationship:

X₂O₃:(n)YO₂, in which X is a trivalent element, boron, iron and/or gallium, and in which X is other than aluminum, will exhibit a lower alpha value than when X is aluminum. The alpha value of the MCM-22 will be at least 1. The alpha value of the aluminum containing species, where X is aluminum can be reduced by base exchanging the protonated or acidic form of the zeolite with an alkali or alkaline earth metal. U.S. Pat. No. 4,652,360 describes alkali metal exchange of a zeolite and is relied upon and incorporated by reference herein for its description. The selectivity of the MCM-22 catalyst may be increased in the double bond isomerization of the olefin and/or the selectivity of the catalysis may be maintained over a wider range of temperatures, with low acidity catalysts. Accordingly, the invention includes the use of an isomerization catalyst containing MCM-22 having an alpha ranging from 1 to 300 and above.

EXAMPLES

1 Examples A and B illustrate the process of the invention.

Examples 1-14 show synthesis and characterization of a catalytic material useful in the present invention, which is commonly referred to as MCM-22.

EXAMPLE A

A sample of H-MCM-22 prepared according to the method outlined in Example 1 was compared with a commercial silica-alumina catalyst, Sorbead W (Kali-Chemie), for olefin isomerization. The properties of Sorbead W are listed below in Table 1.

TABLE 1

| Physical Properties of Sorbead W | |
|---|---|
| Alumina Content | 10 wt % |
| Pore Volume | 0.50 cc/g |
| Pore Diameter | 30 A |
| Surface Area | 750 m²/g |

EXAMPLE B

In a typical experiment, the catalyst was sized to 14/24 mesh and 10 cc were loaded into a ⅜" stainless steel fixed bed micro-unit. The catalyst bed was heated to 800.F with 100 cc/min of dry nitrogen flowing through the unit. The catalyst bed was held at 800° F. for one hour before cooling to 600° F. The unit was pressurized to 50 psig, and a pure 1-butene feed (Matheson) was admitted at 1 gram/gram catalyst/hr. The nitrogen flow was adjusted to give 1/1 mol/mol N₂/HC. The temperature of the reactor was lowered from 600° F., initially, to a final temperature of 300° F. in 100° F. increments. The total effluent from the reactor at each temperature was anlyzed with an on-line gas chromatograph equipped with a 30 meter megabore DB-1 column.

Figure 2:
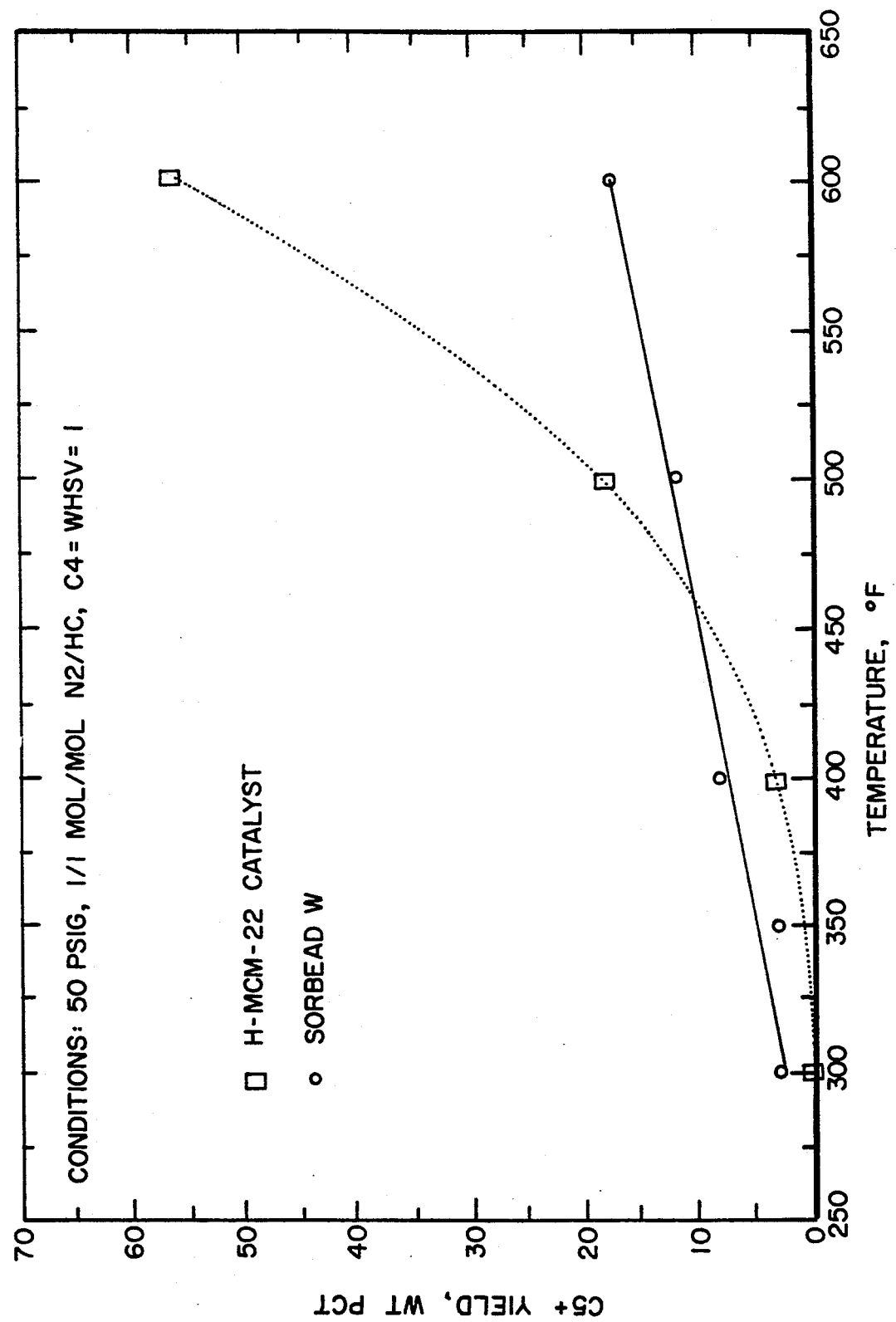
FIG. 2 is a graph of $C_5+$ yield vs. temperature.

The yields of 2-butene from H-MCM-22 and Sorbead W catalysts are plotted as a function of temperature in FIG. 1. Both catalysts produced near equilibrium amounts of 2-butene at about 400° F. However, Sorbead W yielded at best about 80 wt% 2-butenes while H-MCM-22 gave roughly 85 wt% 2-butenes from the 1-butene feed. H-MCM-22 was also found to be more selective at near-equilibrium 2-butene yields. FIG. 2 shows the yield of C₅+ product for both catalysts as a function of temperature. H-MCM-22 produced significantly less heavy products (<5 wt%) from the 1-butene feed at temperatures below 450° F. The reactivity data show that H-MCM-22 can give near-equilibrium amounts of isomerized product from olefinic feeds, and can be more selective than a commercial silica-alumina catalyst, Sorbead W, for olefin isomerization (less C₅+ product).

EXAMPLE 1

One part of sodium aluminate (43.5% Al₂O₃, 32.2% Na₂O, 25.6% H₂O) was dissolved in a solution containing 1 part of 50% NaOH solution and 103.13 parts H₂O. To this was added 4.50 parts hexamethyleneimine. The resulting solution was added to 8.55 parts of Ultrasil, a precipitated, spray-dried silica (about 90% SiO₂).

The reaction mixture had the following composition, in mole ratios:

$SiO_2/Al_2O_3 = 30.0$ $OH^-/SiO_2 = 0.18$ $H_2O/SiO_2 = 44.9$ $Na/SiO_2 = 0.18$ $R/SiO_2 = 0.35$ where R is hexamethyleneimine.

The mixture was crystallized in a stainless steel reactor, with stirring, at least 150° for 7 days. The crystalline product was filtered, washed with water and dried at 120° C. After a 20 hour calcination at 538° C., the X-ray diffraction pattern contained the major lines listed in Table E. The sorption capacities of the calcined material were measured to be:

| H₂O | 15.2 wt. % |
|---|---|
| Cyclohexane | 14.6 wt. % |
| n-Hexane | 16.7 wt. % |

The surface area of the calcined crystalline material was measured to be 494 m²/g.

The chemical composition of the uncalcined material was determined to be as follows:

| Component | wt. % |
|---|---|
| SiO₂ | 66.9 |
| Al₂O₃ | 5.40 |
| Na | 0.03 |
| N | 2.27 |
| Ash | 76.3 |
| SiO₂/Al₂O₃, mole ratio = | 21.1 |

TABLE E

| Degrees 2-Theta | d-Spacing (A) | Interplanar I/I₀ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |

TABLE E-continued

| Degrees 2-Theta | d-Spacing (A) | Interplanar $I/I_o$ |
|---|---|---|
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3-5

Three separate synthesis reaction mixtures were prepared with compositions indicated in Table F. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product crystals were subjected to X-ray diffraction, sorption, surface area and chemical analyses. The results of the sorption, surface area and chemical analyses are presented in Table F. The sorption and surface area measurements were of the calcined product.

TABLE F

| | Example | | |
|---|---|---|---|
| | 3 | 4 | 5 |
| Synthesis Mixture, mole ratios | | | |
| $SiO_2/Al_2O_3$ | 30.0 | 30.0 | 30.0 |
| $OH^-/SiO_2$ | 0.18 | 0.18 | 0.18 |
| $H_2O/SiO_2$ | 19.4 | 19.4 | 44.9 |
| $Na/SiO_2$ | 0.18 | 0.18 | 0.18 |
| $R/SiO_2$ | 0.35 | 0.35 | 0.35 |
| Product Composition, Wt. % | | | |
| $SiO_2$ | 64.3 | 68.5 | 74.5 |
| $Al_2O_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| $SiO_2/Al_2O_3$, mole ratio | 22.5 | 20.9 | 26.0 |
| Adsorption, Wt. % | | | |
| $H_2O$ | 14.9 | 13.6 | 14.6 |
| Cyclohexane | 12.5 | 12.2 | 13.6 |
| n-Hexane | 14.6 | 16.2 | 19.0 |
| Surface Area, $m^2/g$ | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a further preparation of the present zeolite, 4.49 parts of hexamethyleneimine was added to a solution containing 1 part of sodium aluminate, 1 part of 50% NaOH solution and 44.19 parts of $H_2O$. To the combined solution were added 8.54 parts of Ultrasil silica. The mixture was crystallized with agitation at 145° C. for 59 hours and the resultant product was water washed and dried at 120° C.

Product chemical composition (uncalcined), surface area and adsorption analyses results were as set forth in Table G:

TABLE G

| Product Composition | |
|---|---|
| C | 12.1 wt. % |
| N | 1.98 wt. % |
| Na | 640 ppm |
| $Al_2O_3$ | 5.0 wt. % |
| $SiO_2$ | 74.9 wt. % |
| $SiO_2/Al_2O_3$, mole ratio | 25.4 |
| Adsorption, wt. % | |
| Cyclohexane | 9.1 |
| N-Hexane | 14.9 |
| $H_2O$ | 16.8 |
| Surface Area, $m^2/g$ | 479 |

EXAMPLE 8

Twenty-five grams of solid crystal product from Example 7 were calcined in a flowing nitrogen atmospheres at 538° C. for 5 followed by purging with 5% oxygen gas (balance $N_2$) for another 16 hours at 538° C.

Individual 3g samples of the calcined material were ion-exchanged with 100 ml of 0.1 N TEABr, TPABr and $LaCl_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| Ionic Composition, | Exchange Ions | | |
|---|---|---|---|
| wt. % | TEA | TPA | La |
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite has very good stability under severe hydrothermal treatment.

EXAMPLE 11

This example illustrates the preparation of the present zeolite where X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:

| | |
|---|---|
| $SiO_2/B_2O_3 =$ | 6.1 |
| $OH^-/SiO_2 =$ | 0.06 |
| $H_2O/SiO_2 =$ | 19.0 |
| $K/SiO_2 =$ | 0.06 |
| $R/SiO_2 =$ | 0.30 | where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 540° C. and found to have the following sorption capacities:

| | |
|---|---|
| $H_2O$ (12 Torr) | 11.7 wt. % |
| Cyclohexane (40 Torr) | 7.5 wt. % |
| n-Hexane (40 Torr) | 11.4 wt. % |

The surface area of the calcined crystalline material was measured (BET) to be 405m$^2$/g.

The chemical composition of the uncalcined material was determined to be as follows:

| | |
|---|---|
| N | 1.94 wt. % |
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio = | 1406 |
| $SiO_2/(Al + B)_2O_3$, molar ratio = | 25.8 |

EXAMPLE 12

A portion of the calcined crystalline product of Example 11 was treated with $NH_4Cl$ and again calcined. The final crystalline product was tested in the Alpha Test and found to have an Alpha Value of 1.

EXAMPLE 13

This example illustrates another preparation of the zeolite in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

| | |
|---|---|
| $SiO_2/B_2O_3 =$ | 12.3 |
| $OH^-/SiO_2 =$ | 0.056 |
| $H_2O/SiO_2 =$ | 18.6 |
| $K/SiO_2 =$ | 0.056 |
| $R/SiO_2 =$ | 0.30 | where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

| | |
|---|---|
| $H_2O$ (12 Torr) | 14.4 wt. % |
| Cyclohexane (40 Torr) | 4.6 wt. % |
| n-Hexane (40 Torr) | 14.0 wt. % |

The surface area of the calcined crystalline material was measured to be 438m$^2$/g.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio = | 249 |
| $SiO_2/(Al + B)_2O_3$, molar ratio = | 28.2 |

EXAMPLE 14

A portion of the calcined crystalline product of Example 13 was tested in the Alpha Test and found to have an Alpha Value of 5.

EXAMPLE 15

Zeolite MCM-22 was prepared by adding 4.49 parts quantity of hexamethyleneimine to a mixture containing 1.00 part sodium aluminate, 1.00 part 50% NaOH, 8.54 parts Ultrasil VN3 and 44.19 parts deionized $H_2O$. The reaction mixture was heated to 143° C. (290° F.) and stirred in an autoclave at that temperature for crystallization. After full crystallinity was achieved, the majority of the hexamethyleneimine was removed from the autoclave by controlled distillation and the zeolite crystals separated from the remaining liquid by filtration, washed with deionized $H_2O$ and dried.

A portion of the zeolite crystals was combined with $Al_2O_3$ to form a mixture of 65 parts, by weight, zeolite and 35 parts $Al_2O_3$. Water was added to this mixture to allow the resulting catalyst to be formed into extrudates. The catalyst was activated by calcining in nitrogen at 540° C. (1000° F.), followed by aqueous ammonium nitrate exchange and calcining in air at 540° C. (1000° F.).

What is claimed is:
1. A process for isomerizing an isomerizable olefin containing at least four carbon atoms in a feed containing the isomerizable olefin comprising
   contacting said isomerizable olefin with a catalyst composition comprising a synthetic microporous crystalline material, under conditions including a temperature of from about 0° C. to about 650° C., a pressure of from about 1.0 psai to about 2000 psia and a weight hourly space velocity of from 0.1 to about 500 hr$^{-1}$ wherein the synthetic microporous crystalline material is characterized by an X-ray diffraction pattern including values substantially as set forth in Table A of the specification; and recovering an effluent comprising an isomeric olefin which has a number of carbon atoms which is the same number of carbon atoms as in said isomerizable olefin and which has the same number of double bonds as the isomerizable olefin and which is an isomer of said isomerizable olefin, wherein the effluent contains an amount of said isomeric olefin which exceeds any amount of said isomeric olefin in the feed.

2. The process of claim 1, wherein the synthetic microporous crystalline material is characterized by an X-ray diffraction pattern including values substantially as set forth in Table B of the specification.

3. The process of claim 1, wherein the synthetic microporous crystalline material is characterized by an X-ray diffraction pattern including values substantially as set forth in Table C of the specification.

4. The process of claim 1, wherein the synthetic microporous crystalline material is characterized by an X-ray diffraction pattern including values substantially as set forth in Table D of the specification.

5. The process of claim 1, wherein the synthetic microporous crystalline material is characterized by equilibrium adsorption capacities of greater than about 4.5 weight percent for cyclohexane vapor and greater than about 10 weight percent for n-hexane vapor.

6. The process of claim 1, wherein the synthetic microporous crystalline material has an alpha value of at least 1.

7. The process of claim 1, wherein the synthetic microporous crystalline material has an alpha value ranging from 100 to about 300.

8. The process of claim 2, wherein the synthetic microporous crystalline material has an alpha value of at least 1.

9. The process of claim 2, wherein the synthetic microporous crystalline material has an alpha value ranging from 100 to about 300.

10. The process of claim 3, wherein the synthetic microporous crystalline material has an alpha value of at least 1.

11. The process of claim 3, wherein the synthetic microporous crystalline material has an alpha value ranging from 100 to about 300.

12. The process of claim 4, wherein the synthetic microporous crystalline material has an alpha value of at least 1.

13. The process of claim 4, wherein the synthetic microporous crystalline material has an alpha value ranging from 100 to about 300.

14. The process of claim 4, wherein the synthetic microporous crystalline material has a composition expressed as the molar relationship $$X_2O_c:(n)YO_2$$

wherein n is at least about 10, X is selected from the group consisting of aluminum, boron, gallium and combinations thereof and Y is selected from the group consisting of silicon, germanium and admixtures thereof and O is oxygen.

15. The process of claim 1, wherein the synthetic microporous crystalline material has a composition expressed as the molar relationship $$X_2O_3:(n)YO_2$$

wherein n is at least about 10, X is selected from the group consisting of aluminum, boron, gallium and combinations thereof and Y is selected from the group consisting of silicon, germanium and admixtures thereof and O is oxygen.

16. The process of claim 1, wherein said conditions include a temperature of from about 100° C. to about 650° C., a pressure of from about 14 psia to about 500 psia and a weight hourly space velocity of 0.1 to 100 $hr^{-1}$.

17. The process of claim 6, wherein said conditions include a temperature of from about 100° C. to about 650° C., a pressure of from about 14 psia to about 500 psia and a weight hourly space velocity of 0.1 to 100.

18. The process of claim 1, wherein the catalyst composition contains a dehydrogenation/hydrogenation metal.

19. The process of claim 2, wherein the catalyst composition contains a dehydrogenation/hydrogenation metal.

20. The process of claim 3, wherein the catalyst composition contains a dehydrogenation/hydrogenation metal.

21. The process of claim 4, wherein the catalyst composition contains a dehydrogenation/hydrogenation metal.

22. The process of claim 6, wherein the catalyst composition contains a dehydrogenation/hydrogenation metal.

23. The process of claim 1, wherein the isomerizable olefin is 1-butene.

24. The process of claim 23, wherein the isomeric olefin is 2-butene.

25. The process of claim 1, wherein the isomerizable olefin is 1-butene, cis-2-butene trans-1-butene, and/or mixtures thereof.

26. The process of claim 25, wherein the isomeric olefin is isobutylene.

27. The process of claim 26, wherein the conditions include a temperature of from about 100° C. to about 650° C., a pressure of from 14 psia to about 500 psia and a weight hourly space velocity of 0.1 to 100 $hr^{-1}$.

28. A process for upgrading a petroleum derived fraction having a boiling point range up to about 390° F. and containing an isomerizable olefin containing at least four carbon atoms, wherein the process comprises contacting said fraction with a catalyst composition comprising a synthetic microporous crystalline material, under conditions including a temperature of from about 0° C. to about 650° C., a pressure of from about 1.0 psia to about 2000 psia and a weight hourly space velocity of from 0.1 to about 500 $hr^{-1}$ wherein the synthetic microporous crystalline material is characterized by an X-ray diffraction pattern including values substantially as set forth in Table A of the specification; and recovering an effluent comprising an isomeric olefin which has a number of carbon atoms which is the same number of carbon atoms as in said isomerizable olefin and which has the same number of double bonds as the isomerizable olefin and which is an isomer of said isomerizable olefin, wherein the effluent contains an amount of said isomeric olefin which exceeds any amount of said isomeric olefin in the feed.

29. The process of claim 28, wherein the synthetic microporous crystalline material is characterized by an X-ray diffraction pattern including values substantially as set forth in Table B of the specification.

30. The process of claim 28, wherein the synthetic microporous crystalline material is characterized by an x-ray diffraction pattern including values substantially as set forth in Table C of the specification.

31. The process of claim 28, wherein the synthetic microporous crystalline material is characterized by an X-ray diffraction pattern including values substantially as set forth in Table D of the specification.

32. The process of claim 28, wherein the synthetic microporous crystalline material is characterized by equilibrium adsorption capacities of greater than about 4.5 weight percent for cyclohexane vapor and greater than about 10 weight percent for n-hexane vapor.

33. The process of claim 28, wherein the synthetic microporous crystalline material has an alpha value of at least 1.

34. The process of claim 28, wherein the synthetic microporous crystalline material has an alpha value ranging from 100 to about 300.

35. The process of claim 29, wherein the synthetic microporous crystalline material has an alpha value of at least 1.

36. The process of claim 29, wherein the synthetic microporous crystalline material has an alpha value ranging from 100 to about 300.

37. The process of claim 30, wherein the synthetic microporous crystalline material has an alpha value of at least 1.

38. The process of claim 30, wherein the synthetic microporous crystalline material has an alpha value ranging from 100 to about 300.

39. The process of claim 31, wherein the synthetic microporous crystalline material has an alpha value of at least 1.

40. The process of claim 31, wherein the synthetic microporous crystalline material has an alpha value ranging from 100 to about 300.

41. The process of claim 28, wherein said conditions include a temperature of from about 100° C. to about 650° C., a pressure of from about 14 psia to about 500 psia and a weight hourly space velocity of 0.1 to 100 $hr^{-1}$.

42. The process of claim 33, wherein said conditions include a temperature of from about 100° C. to a about 650° C., a pressure of from about 14 psia to about 500 psia and a weight hourly space velocity of 0.1 to 100.

43. The process of claim 28, wherein the catalyst composition contains a dehydrogenation/hydrogenation metal.

44. The process of claim 29, wherein the catalyst composition contains a dehydrogenation/hydrogenation metal.

45. The process of claim 30, wherein the catalyst composition contains a dehydrogenation/hydrogenation metal.

46. The process of claim 31, wherein the catalyst composition contains a dehydrogenation/hydrogenation metal.

47. The process of claim 28, wherein the isomerizable olefin is 1-butene.

48. The process of claim 47, wherein the isomeric olefin is 2-butene.

49. The process of claim 28, wherein the isomerizable olefin is 1-butene, cis-2-butene trans-1-butene, and/or mixtures thereof.

50. The process of claim 49, wherein the isomeric olefin is isobutylene.

* * * * *

UNITED STATES PATENT AND TRADEMARK OFFICE
CERTIFICATE OF CORRECTION

PATENT NO. : 5,107,047

DATED : April 21, 1992

INVENTOR(S) : Kenneth J. Del Rossi

It is certified that error appears in the above-identified patent and that said Letters Patent is hereby corrected as shown below:

Column 14, line 66 (claim 1), delete "psai" and insert --psia--.

Column 15, line 58 (claim 14), in the formula, change the "e" to a --3--.

Column 16, line 41 (claim 27), "the" should read --said--.

Column 18, line 11 (claim 41), "$hr^{31}$ $^1$" should read --$hr^{-1}$--.

Signed and Sealed this

Third Day of August, 1993

Attest:

MICHAEL K. KIRK

*Attesting Officer*     *Acting Commissioner of Patents and Trademarks*